US012741276B2

United States Patent
(12) United States Patent
Wattanakit et al.

(10) Patent No.: US 12,741,276 B2
(45) Date of Patent: Sep. 22, 2026

(54) CATALYST FOR PRODUCING LIGHT OLEFINS FROM CATALYTIC CRACKING OF HYDROCARBON HAVING 4 TO 7 CARBON ATOMS AND A PROCESS FOR PRODUCING LIGHT OLEFINS BY USING A CATALYST THEREOF

(71) Applicant: PTT Global Chemical Public Company Limited, Chatuchak (TH)

(72) Inventors: Chularat Wattanakit, Chatuchak (TH); Chadatip Rodaum, Chatuchak (TH); Anawat Thivasasith, Chatuchak (TH); Sitthiphong Pengpanich, Chatuchak (TH); Kaew-Arpha Thavornprasert, Chatuchak (TH)

(73) Assignee: PTT Global Chemical Public Company Limited, Chatuchak (TH)

( * ) Notice: Subject to any disclaimer, the term of this patent is extended or adjusted under 35 U.S.C. 154(b) by 202 days.

(21) Appl. No.: 17/788,184

(22) PCT Filed: Dec. 23, 2020

(86) PCT No.: PCT/IB2020/062373
§ 371 (c)(1),
(2) Date: Jun. 22, 2022

(87) PCT Pub. No.: WO2021/130686
PCT Pub. Date: Jul. 1, 2021

(65) Prior Publication Data
US 2023/0038518 A1 Feb. 9, 2023

(30) Foreign Application Priority Data
Dec. 27, 2019 (TH) ................................ 1901008206

(51) Int. Cl.
*B01J 29/89* (2006.01)
*B01J 29/04* (2006.01)
(Continued)

(52) U.S. Cl.
CPC ............. *B01J 29/89* (2013.01); *B01J 29/047* (2013.01); *B01J 29/86* (2013.01); *B01J 35/643* (2024.01);
(Continued)

(58) Field of Classification Search
CPC ............ C07C 2529/04; C07C 2529/86; C07C 2529/89; C07C 4/06; B01J 29/047;
(Continued)

(56) References Cited

U.S. PATENT DOCUMENTS 4,000,248 A 12/1976 Martin
5,053,374 A 10/1991 Absil et al.
(Continued)

FOREIGN PATENT DOCUMENTS

WO 2014074492 A1 5/2014
WO 2019088935 A1 5/2019
WO 2020218980 A1 10/2020

OTHER PUBLICATIONS

International Search Report and Written Opinion issued in International Application No. PCT/IB2020/062373 dated May 13, 2021.
(Continued)

*Primary Examiner* — Smita S Patel
(74) *Attorney, Agent, or Firm* — Troutman Pepper Locke LLP

(57) ABSTRACT

The present invention relates to a catalyst for producing light olefins from catalytic cracking of hydrocarbon having 4 to 7 carbon atoms, wherein said catalyst comprises zeolite having the ring arrangement of 8 to 10 silicon atoms and hierarchical zeolite comprising 0.1 to 2 nm of micropore, 2
(Continued)

to 50 nm of mesopore, and greater than 50 nm of macropore, wherein the mesopore and macropore are greater than or equal to 40% when comparing to total pore volume, and said catalyst comprises element having $2^+$ to $4^+$ oxidation state with 0.1 to 3% by weight of the catalyst.

9 Claims, 5 Drawing Sheets

(51) Int. Cl.
*B01J 29/86* (2006.01)
*B01J 35/64* (2024.01)
*B01J 35/66* (2024.01)
*C07C 4/06* (2006.01)

(52) U.S. Cl.
CPC ........... *B01J 35/647* (2024.01); *B01J 35/651* (2024.01); *B01J 35/695* (2024.01); *C07C 4/06* (2013.01); *C07C 2529/04* (2013.01); *C07C 2529/86* (2013.01); *C07C 2529/89* (2013.01)

(58) Field of Classification Search
CPC ............ B01J 29/86; B01J 29/00; B01J 29/04; B01J 35/643; B01J 35/647; B01J 35/651
See application file for complete search history.

(56) References Cited

U.S. PATENT DOCUMENTS 6,222,087 B1 4/2001 Johnson et al.
7,981,273 B2 7/2011 Nicholas et al.
8,157,985 B2 4/2012 Nicholas et al.
10,427,142 B1 10/2019 Al-Herz et al.
2003/0171634 A1 9/2003 Corma
2005/0070422 A1 3/2005 Chen et al.
2010/0105974 A1 4/2010 Towler et al.
2015/0018590 A1 1/2015 Stevenson et al.
2021/0322961 A1* 10/2021 Wattanakit ............... B01J 35/58

OTHER PUBLICATIONS

P. Wuamprakhon et al., "Direct synthesis of hierarchical ferrierite nanosheet assemblies via an organosilane template approach and determination of their catalytic activity." Microporous and Mesoporous Materials, vol. 219, pp. 1-9 (2016).

T. Komatsu et al., "Selective formation of alkenes through the cracking of n-heptane on Ca2+-exchanged ferrierite." Applied Catalysis A: General, vol. 214, Issue 1, pp. 103-109 (2001).

R. K. Ahedi et al., "Studies in the Crystallization of Ferrierite (FER) Type Zeolites in Presence of Promoting Medium." Journal of Porous Materials, vol. 4, pp. 171-179 (1997).

A. Thivasasith et al. "Nanocavity effects of various zeolite frameworks on n-pentane cracking to light olefins: combination studies of DFT calculations and experiments." Phys. Chem. Chem. Phys., vol. 21, p. 22215-22223 (2019).

Xu Hou et al., "Superiority of ZrO2 surface enrichment on ZSM-5 zeolites in n-pentane catalytic cracking to produce light olefins." Microporous and Mesoporous Materials, vol. 276, pp. 41-51 (2019).

F. Momayez et al., "Synthesis of zirconium and cerium over HZSM-5 catalysts for light olefins production from naphtha." Journal of Analytical and Applied Pyrolysis, vol. 112, pp. 135-140 (2015).

* cited by examiner

CATALYST FOR PRODUCING LIGHT OLEFINS FROM CATALYTIC CRACKING OF HYDROCARBON HAVING 4 TO 7 CARBON ATOMS AND A PROCESS FOR PRODUCING LIGHT OLEFINS BY USING A CATALYST THEREOF

This application is a U.S. national stage application of International Application No. PCT/IB2020/062373, filed on Dec. 23, 2020, which claims priority from Thailand Application No. 1901008206, filed Dec. 27, 2019. The entire contents of each application are hereby incorporated by reference in their entirety.

TECHNICAL FIELD

The present invention relates to the field of chemistry, in particular, to the catalyst for producing light olefins from catalytic cracking of hydrocarbon having 4 to 7 carbon atoms and a process for producing light olefins by using a catalyst thereof.

BACKGROUND ART

In the production industry of light olefins which are ethylene and propylene popularly used as the important precursors in the production of many important polymers such as polyethylene and polypropylene, the production methods being used is the cracking of the precursor such as ethane or naphtha compounds separated from natural gas by the thermal steam cracking process. However, this process is operated at very high temperature (800-900° C.), thus requiring high production energy. Moreover, although this production process can produce high amount of light olefins especially ethylene, it provides high amount of unwanted by-products which are light hydrocarbons such as methane, ethane, and propane, and heavy hydrocarbons which contain more than 9 carbon atoms that can occur the accumulation or the so-called coking with high amount in the production process. Therefore, the production process needs to be stopped in order to maintain the reactor regularly. In light of the above, in order to improve the production of light olefins to be more selective and in order to reduce temperature and energy used in the production, reduce the coking, and reduce the frequent reactor maintenance, the production of light olefins using naphtha compound as precursor by suitable chemical catalyst for the catalytic cracking reaction can reduce the temperature and energy, and is capable of the production of light olefins with high amount. These obtained results are very important in the industry and have less harmful effects on the environment comparing to the conventional production.

Until now, there has been studies and development on the zeolite compound because of its good chemical and physical properties such as acidity-basicity, which is adjustable according to reaction interested, thermal and chemical stability, and shape selectivity. Because of these properties, zeolite has been applied in various works such as adsorbent, ion exchanger, and heterogeneous catalyst.

In order to provide the production of light olefins by catalytic cracking reaction occurring with highest efficacy, the zeolite catalyst used must give highest selectivity to the interested olefins comparing to the by-product from the side reactions, especially the light alkane products such as methane, ethane, and propane, aromatic compounds, and coking. Therefore, the zeolite catalyst used in said process has been developed continuously in terms of high selectivity to olefin products and development of the catalyst to reduce catalyst deactivation etc.

For the production process of the light olefins from naphtha compound by catalytic cracking reaction on suitable catalyst, the researchers from Honeywell UOP LLC (U.S. Pat. Nos. 7,981,273B2 8,157,985B2, and US20100105974A1) had developed the suitable catalyst in which the developed catalyst was in the group of aluminosilicate or zeolite. This catalyst group was modified by adding potassium, sodium, gallium, and organoammonium cation compound. The organoammonium cation compound was ethyl trimethyl ammonium (ETMA), diethyl dimethyl ammonium (DEDMA), and tetraethyl ammonium (TEA) etc. Moreover, they also studied and developed various aluminosilicate or zeolite catalysts such as chabazite, erionite, ferrierite, and ZSM-22 etc. to mix with the second group of catalyst which was nano-silicalite at the silica to alumina ratio greater than 200.

The researchers from ExxonMobil Oil Corporation (U.S. Pat. No. 6,222,087B1 and US20050070422A1) had studied and developed the catalyst for production of light olefins using hydrocarbon compound having 4 to 7 carbon atoms as the precursor. The studied and developed catalysts were various zeolite catalysts such as ZSM-22, ZSM-35, SAPO-34, ZSM-5, and ZSM-11, including zeolite having silica to alumina ratio greater than 300. Moreover, they had modified the zeolite catalyst to be efficient in the production of light olefins to be more selective and reduce the unwanted by-products such as light alkanes, including aromatic compounds and coking, by adding phosphorous and metal oxide such as gallium, titanium, and zirconia.

Nevertheless, the use of conventional zeolites, that has not been modified in their pore size, acidity, and suitable active sites, in the industry has limitations such as poor catalytic efficacy, fast deactivation, and difficulty and complication in catalyst regeneration. The main reason that gives limitation to the conventional zeolite is the limitation in mass transfer and diffusion due to pore size in zeolite structure having small size with angstroms level. The large structure of zeolite crystal causes the critical mass transfer status which results in the difficulty of the precursor molecules to get into the active sites and leads to the high risk in causing catalyst deactivation by coking due to the recombination reaction of intermediates. Moreover, there also have other limitations of the use of conventional zeolite in the production of light olefins by catalytic cracking reaction of hydrocarbon compound in order to provide high selectivity to light olefins such as the product formation from side reactions at the active sites on the outer surface.

The development of the hierarchical zeolite catalyst comprising the small pores and having the ring arrangement of 8 to 10 silicon atoms is important and very specific in the production of light olefins from naphtha compound by catalytic cracking process. The patent documents related to the invention of the hierarchical zeolite catalyst comprising small pores are the following. Patent document WO2014074492A1 discloses the preparation of said zeolite catalyst which was ferrierite zeolite having small crystal about 200 nm which is prepared from precursor comprising silica, alumina, and alkali metal, and 2 types of organic structure-directing agents (OSDA) in which the first one was tetramethyl ammonium and the second one was pyrrolidine, 1,3-diaminopropane, 1-methylpyrrolidine, piperidine, pyridine, ethylene diamine, or 1,4-diaminobutane. Moreover, patent document U.S. Pat. No. 4,000,248 confirms and discloses that the organic structure-directing agent containing nitrogen is popularly used as the structure-directing agent in the synthesis of ferrierite zeolite catalyst having high purity. Moreover, this can reduce the temperature and time used in the synthesis and have the crystal size about 500 nm when comparing to the absence of organic structure-directing agent.

Moreover, the research work from R. Ahedi et al. (J. Porous Mater. 4 (1997) 171-179) discloses the preparation of the ferrierite zeolite catalyst from the precursor containing silica and alumina, and organic structure-directing agent which was pyrrolidine. This resulted in the ferrierite zeolite catalyst having purity, having large structure at about 10 μm, and having various structures. Next, the research work from P. Wuamprakhon et al. (Micropor. Mesopor. Mater. 219 (2016) 1-9) discloses the modification in the synthesis of ferrierite zeolite catalyst to have nano-sheet crystal characteristic using the precursor containing silica and alumina, the organic structure-directing agent which was pyrrolidine, the template substance to obtain the ferrierite zeolite crystal having ordered nano-sheet structure which was dimethyloctadecyl[3-(trimethoxysilyl)propyl]ammonium chloride (TPOAC), and the silica to alumina ratio greater than 20 to 30. However, said work does not disclose the use in the catalytic cracking process.

From all above, the research work from A. Thivasasith et al. (Phys. Chem. Chem. Phys., 21 (2019) 22215-22223) discloses the use of different zeolites for the catalytic cracking process of pentane to ethylene and propylene. The zeolites used in this study were ferrierite, ZSM-5, and faujasite. From the study, it discloses that ferrierite zeolite having smallest pore size could produce highest ethylene and propylene when comparing to said other zeolites.

Moreover, there have been disclosures about the catalytic cracking process that converts hydrocarbon compound having 5 carbon atoms to light olefins on the metal added onto ZSM-5 zeolite, in which Xu Hou et al. (Micropor. Mesopor. Mater. 276 (2019) 41-51) discloses that the zirconium (Zr) catalyst on ZSM-5 zeolite showed good efficacy in the production of light olefins and the modification of zeolite catalyst by adding such zirconium metal could be done by impregnation and chemical liquid deposition (CLD) methods. The test for catalytic efficacy was performed at the temperature of 550° C. The catalyst could convert 73% of the hydrocarbon compound having 5 carbon atoms to other products and had the selectivity to ethylene of 18%, propylene of 28%, and butene of 13%. Moreover, there also have the modification of zeolite by adding other metals. The work from F. Momayez et al. (J. Anal. Appl. Phyrro. 112 (2015) 135-140) discloses the preparation and modification of the metal catalyst on zeolite for the cracking reaction of hydrocarbon compound having 5 carbon atoms. The metal was added into zeolite by impregnation method and the metal types added were cerium and zirconium. The catalyst efficacy was tested at the temperature of 600 to 700° C. It was found that the addition of zirconium metal on zeolite yielded 20% of ethylene production and 37% of propylene production.

From all reasons said above, this invention aims to prepare the hierarchical zeolite catalyst having the ring arrangement of 8 to 10 silicon atoms, and having mole ratio of silica to alumina ($SiO_2/Al_2O_3$) from 20 to 80 for the production of light olefins from catalytic cracking of the hydrocarbon having 4 to 7 carbon atoms, wherein said catalyst structure provides better flow of hydrocarbon, and after the catalytic cracking, the small pore size of the zeolite can control the product to have the selectivity to light olefins, including the reduction of coking or hydrocarbon having more than 9 carbon atoms that clogs within the zeolite pore. This makes this catalyst to have longer life in usage.

SUMMARY OF INVENTION

The present invention relates to the catalyst for producing light olefins from catalytic cracking of hydrocarbon having 4 to 7 carbon atoms and a process for producing light olefins by using a catalyst thereof, wherein said catalyst comprises zeolite having the ring arrangement of 8 to 10 silicon atoms and hierarchical zeolite comprising 0.1 to 2 nm of micropore, 2 to 50 nm of mesopore, and greater than 50 nm of macropore, wherein the mesopore and macropore are greater than or equal to 40% when comparing to total pore volume, and said catalyst comprises element having $2^+$ to $4^+$ oxidation state with 0.1 to 3% by weight of the catalyst.

DESCRIPTION OF THE INVENTION

Figure 1:
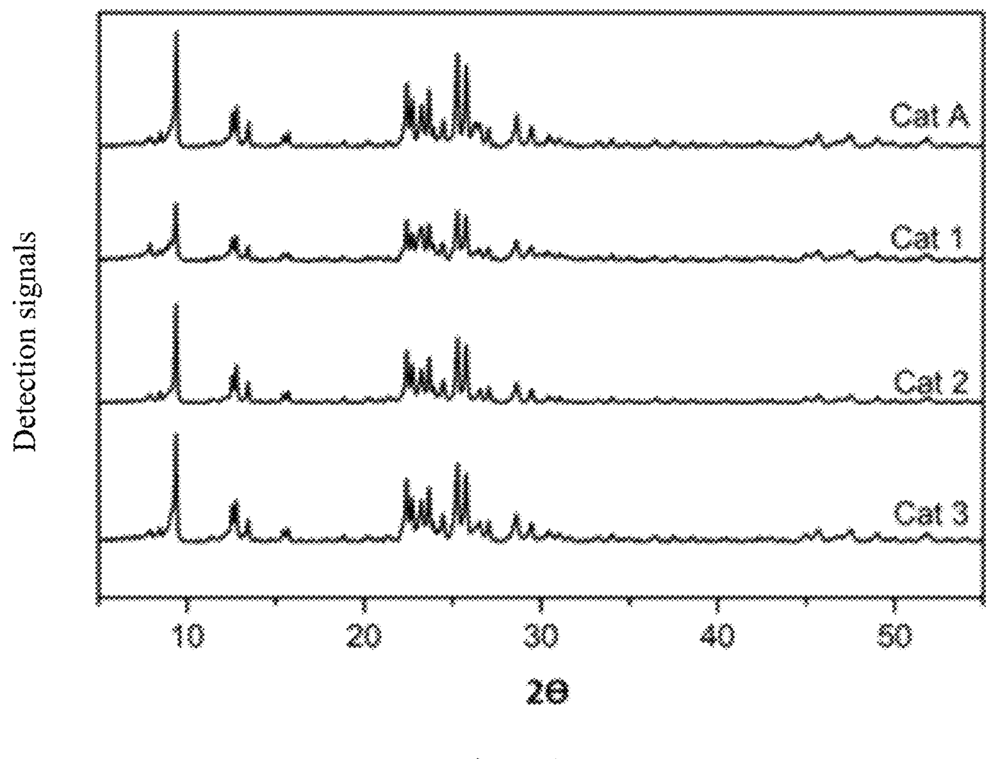
FIG. 1 shows the specific characteristic of the crystal of the sample according to the invention and the comparative sample.

The present invention relates to the catalyst for producing light olefins from catalytic cracking of hydrocarbon having 4 to 7 carbon atoms and a process for producing light olefins by using a catalyst thereof, which will be described in the following aspects of the invention.

Any aspect being described herein also means to include the application to other aspects of this invention unless stated otherwise.

Technical terms or scientific terms used herein have definitions as understood by an ordinary person skilled in the art unless stated otherwise.

Any tools, equipment, methods, or chemicals named herein mean tools, equipment, methods, or chemicals being operated or used commonly by those person skilled in the art unless stated otherwise that they are tools, equipment, methods, or chemicals specific only in this invention.

Use of singular noun or singular pronoun with “comprising” in claims or specification means “one” and also including “one or more”, “at least one”, and “one or more than one”.

All compositions and/or methods disclosed and claims in this application are intended to cover embodiments from any operation, performance, modification, or adjustment any factors without any experiment that significantly different from this invention, and obtain with object with utility and resulted as same as the present embodiment according to person ordinary skilled in the art although without specifically stated in claims. Therefore, substitutable or similar object to the present embodiment, including any minor modification or adjustment that can be apparent to person skilled in the art should be construed as remains in spirit, scope, and concept of invention as appeared in appended claims.

Throughout this application, term “about” means any number that appeared or expressed herein that could be varied or deviated from any error of equipment, method, or personal using said equipment or method.

Hereafter, invention embodiments are shown without any purpose to limit any scope of the invention.

The present invention relates to the catalyst for producing light olefins from catalytic cracking of hydrocarbon having 4 to 7 carbon atoms, wherein said catalyst comprises zeolite having the ring arrangement of 8 to 10 silicon atoms and hierarchical zeolite comprising 0.1 to 2 nm of micropore, 2 to 50 nm of mesopore, and greater than 50 nm of macropore, wherein the mesopore and macropore are greater than or equal to 40% when comparing to total pore volume, and said catalyst comprises element having $2^+$ to $4^+$ oxidation state with 0.1 to 3% by weight of the catalyst.

In one aspect of the invention, the zeolite according to the invention has pore size of 0.35 nm to 0.54 nm.

Preferably, said hierarchical zeolite comprises micropore having size in the range of 0.35 to 0.54 nm and mesopore having size in the range of 2 to 10 nm, wherein the mesopore is greater than or equal to 40% when comparing to total pore volume. Most preferably, the mesopore is 40 to 60% when comparing to total pore volume.

In one aspect of the invention, zeolite having the ring arrangement of 8 to 10 silicon atoms is ferrierite.

In one aspect of the invention, zeolite has the mole ratio of silica to alumina from 20 to 60.

In one aspect of the invention, element having $2^+$ to $4^+$ oxidation state is selected from germanium, zirconium, or boron, preferably germanium.

In one aspect of the invention, said element is in the amount of 0.1 to 3% by weight of the catalyst, preferably in the amount of 0.2 to 1% by weight of the catalyst.

In one aspect of the invention, the catalyst according to the invention may be prepared by the following steps:

(a) preparing the solution containing the alumina compound, silica compound, and the soft structure-directing agents;
(b) subjecting the mixture obtained from step (a) to the hydrothermal process at the determined temperature and time in order to make said mixture to form the hierarchical zeolite; and
(c) drying the hierarchical zeolite from step (b);

wherein the soft structure-directing agents in step (a) are pyrrolidine and 3-(trimethoxysilyl)-propyl-octadecyl-dimethyl-ammonium chloride (TPOAC);

wherein the soft structure-directing agent in step (a) is quaternary ammonium salt containing silane group.

In one aspect of the invention, in step (a), the compound for preparing zeolite is the mixture of alumina compound selected from aluminum isopropoxide, sodium aluminate, or aluminium sulfate, and silica compound selected from tetraethyl orthosilicate, sodium silicate, or silica gel.

In one aspect of the invention, step (a) may further comprise the precursor compound of element having $2^+$ to $4^+$ oxidation state that may be selected from germanium oxide, germanium chloride, zirconium oxychloride, zirconyl nitrate, or boric acid.

In one aspect of the invention, step (b) is operated at the temperature in the range of about 130 to 180° C. for 3 to 6 days.

In another aspect, said catalyst preparation process may further comprise the steps of drying and calcination.

Drying may be performed by conventional drying method using oven, vacuum drying, stirred evaporation, and drying by rotary evaporator.

Calcination may be performed under atmospheric condition for about 4 to 10 hours, and the temperature in the range of about 400 to 650° C., preferably about 4 to 6 hours and the temperature in the range of about 550 to 600° C.

In another aspect of the invention, the present invention relates to the process for producing light olefins, comprising contact of hydrocarbon compound having 4 to 7 carbon atoms to the catalyst at the temperature of about 550 to 650° C. and the pressure of about 1 to 3 bars, wherein the catalyst is selected from catalyst according to the invention as described above.

In one aspect of the invention, the hydrocarbon compound having 4 to 7 carbon atoms can be selected from butane, pentane, hexane and heptane.

In one aspect of the invention, the catalytic cracking may be operated in fixed bed system, moving bed system, fluidized bed system, or batch system.

The weight hourly space velocity (WHSV) of the feed line of the hydrocarbon compound in the catalytic cracking is in the range of about 1 to 6.5 per hour, preferably in the range of about 2 to 5 per hour.

Generally, any person skilled in this art can adjust the catalytic cracking condition to be suitable for type and composition of feed line, catalyst, and reactor system.

The following examples are only for demonstrating one aspect of this invention, not for limiting the scope of this invention in any way.

Preparation of the Catalyst

The preparation of the catalyst according to the invention can be done by the following methods.

Preparation of the Hierarchical Zeolite Containing Element Having $2^+$ to $4^+$ Oxidation State in its Structure The solution containing aluminum sulfate and sodium silicate was prepared with the mole ratio of silica to alumina about 44 and using pyrrolidine and trimethoxysilyl-propyl-octadecyl-dimethyl-ammonium chloride as the structure-directing agents of the zeolite. The addition of element having $2^+$ to $4^+$ oxidation state by in-situ method could be done by adding precursor compound of the desired element with the ratio of desired element to zeolite of about 0.2-1% by weight into the mixture of alumina compound, silica compound, and structure-directing agents. Then, the obtained mixture was subjected to the hydrothermal process at the temperature about 130-180° C. for about 3-6 days in order to make said mixture to form the zeolite.

Then, the obtained zeolite was washed with deionized water until the pH of washed water was less than 9. The obtained substance was dried at the temperature about 100-200° C. for 12-24 hours. Then, the substance was calcined in order to remove the structure-directing agents at the temperature about 500-650° C. for about 8-12 hours. The hierarchical zeolite was obtained as white powder.

Then, the ion exchange was performed on the synthesized zeolite catalyst by dissolving the obtained zeolite in about 0.1 M of ammonium nitrate solution ($NH_4NO_3$) at the temperature about 80° C. The mixture was stirred for about 2 hours and washed with purified water, and then the zeolite was dried. Then, the zeolite was calcined at the temperature about 550° C. for about 6 hours.

Comparative Sample Cat A

The comparative sample Cat A is the conventional ferrierite zeolite prepared with the solution containing aluminum sulfate and sodium silicate. The mole ratio of silica to alumina was 44 and only pyrrolidine was used as the structure-directing agent of the zeolite. Then, the obtained mixture was subjected to the hydrothermal process at the temperature about 130-180° C. for about 3-6 days in order to make said mixture to form the zeolite. Then, the zeolite catalyst synthesized was washed and subjected to ion exchange by dissolving the obtained zeolite in about 0.1 M of ammonium nitrate solution ($NH_4NO_3$) at the temperature about 80° C. The mixture was stirred for about 2 hours and washed with purified water, and then the zeolite was dried. Then, the zeolite was calcined at the temperature about 550° C. for about 6 hours.

Sample According to the Invention Cat 1

The sample according to the invention Cat 1 was prepared by the method described for the preparation of the hierarchical zeolite using zirconyl nitrate as the precursor compound in order to contain zirconium in the catalyst composition with ratio of zirconium to zeolite about 0.2% by weight.

Sample According to the Invention Cat 2

The sample according to the invention Cat 2 was prepared by the method described for the preparation of the hierarchical zeolite using boric acid as the precursor compound in order to contain boron in the catalyst composition with ratio of boron to zeolite about 0.5% by weight.

Sample According to the Invention Cat 3

The sample according to the invention Cat 3 was prepared by the method described for the preparation of the hierarchical zeolite using germanium oxide as the precursor compound in order to contain germanium in the catalyst composition with ratio of germanium to zeolite about 0.2% by weight.

Sample According to the Invention Cat 4

The sample according to the invention Cat 4 was prepared by the method described for the preparation of the hierarchical zeolite using germanium oxide as the precursor compound in order to contain germanium in the catalyst composition with ratio of germanium to zeolite about 0.5% by weight.

Sample According to the Invention Cat 5

The sample according to the invention Cat 5 was prepared by the method described for the preparation of the hierarchical zeolite using germanium oxide as the precursor compound in order to contain germanium in the catalyst composition with ratio of germanium to zeolite about 1% by weight.

Testing of the Catalytic Cracking of the Hydrocarbon Having 4 to 7 Carbon Atoms for Producing Light Olefins as Product The testing of catalytic cracking of the hydrocarbon having 4 to 7 carbon atoms for the production of light olefins may be performed under the following conditions.

The catalytic cracking was operated in the fixed bed reactor using about 0.5 g of the catalyst. Prior to the reaction, the catalyst was contacted with the mixed gases of hydrogen in helium having flow rate about 40 mL/min for about 3 hours. Then, the hydrocarbon having 5 carbon atoms was fed with the flow rate about 1 g/hour. The reaction was operated at the temperature about 600-625° C. under atmospheric pressure and the weight hourly space velocity (WHSV) was about 2 per hour.

Then, the reaction was monitored by measuring the change of reactant and the formation of product compositions after subjecting to the catalyst at any time with using gas chromatography technique equipped with the outlet of the fixed bed reactor, and using flame ionization detector (FID) as the detector and GASPRO capillary column for separating analysis of each composition of said compound.

FIG. 1 shows the specific characteristic of the crystal of the sample according to the invention and the comparative sample which shows the ferrierite zeolite structure.

Figure 2:
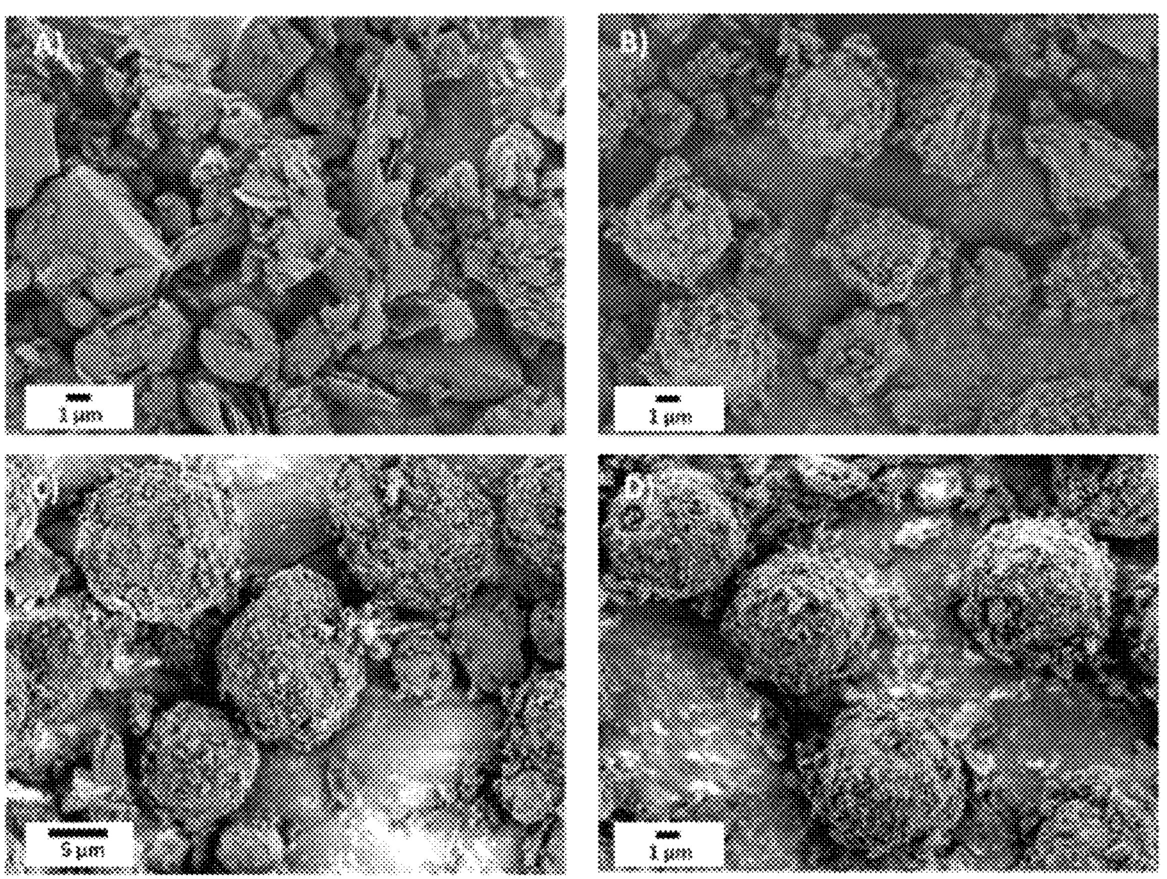
FIGS. 2A), B), C), and D) show results from the scanning electron microscope of the comparative sample A, the sample according to the invention 1, 2, and 3, respectively.

Moreover, in order to show the crystal structure, the scanning electron microscope (SEM) was used to analyze as shown in FIG. 2 which shows that the comparative sample Cat A had no certain characteristic of the crystal, but the sample according to the invention had spherical crystal having crystal size in the range of 3-6 μm and being more porous than the comparative sample.

Table 1 shows the physical properties of the comparative sample and the sample according to the invention. According to the result, it was found that the zeolite prepared from the invention had hierarchical pores comprising micropore and mesopore, wherein the mesopore was greater than or equal to 40% when comparing to total pore volume and had amount more than the conventional zeolite. Moreover, in order to show the characteristic of crystal structure, the scanning electron microscope (SEM) was used to analyze. The results were showed in FIG. 2 which shows that the zeolite according to the invention had hierarchical pores comprising rough surface when compared to the conventional zeolite.

TABLE 1

Specific surface area and porous properties of the comparative sample and the sample according to the invention

| Sample | Specific surface area ($S_{BET}$) ($m^2/g$) | External surface area ($S_{ext}$) ($m^2/g$) | Total pore volume ($V_{total}$) ($cm^3/g$) | Mesopore volume ($V_{meso}$) ($cm^3/g$) | Percentage of mesopore volume (%) |
|---|---|---|---|---|---|
| Comparative sample Cat A | 341 | 12 | 0.16 | 0.03 | 18 |
| Sample according to the invention CAT1 | 236 | 59 | 0.21 | 0.12 | 58 |
| Sample according to the invention CAT2 | 300 | 55 | 0.22 | 0.10 | 45 |
| Sample according to the invention CAT3 | 218 | 52 | 0.20 | 0.11 | 57 |

Figure 3:
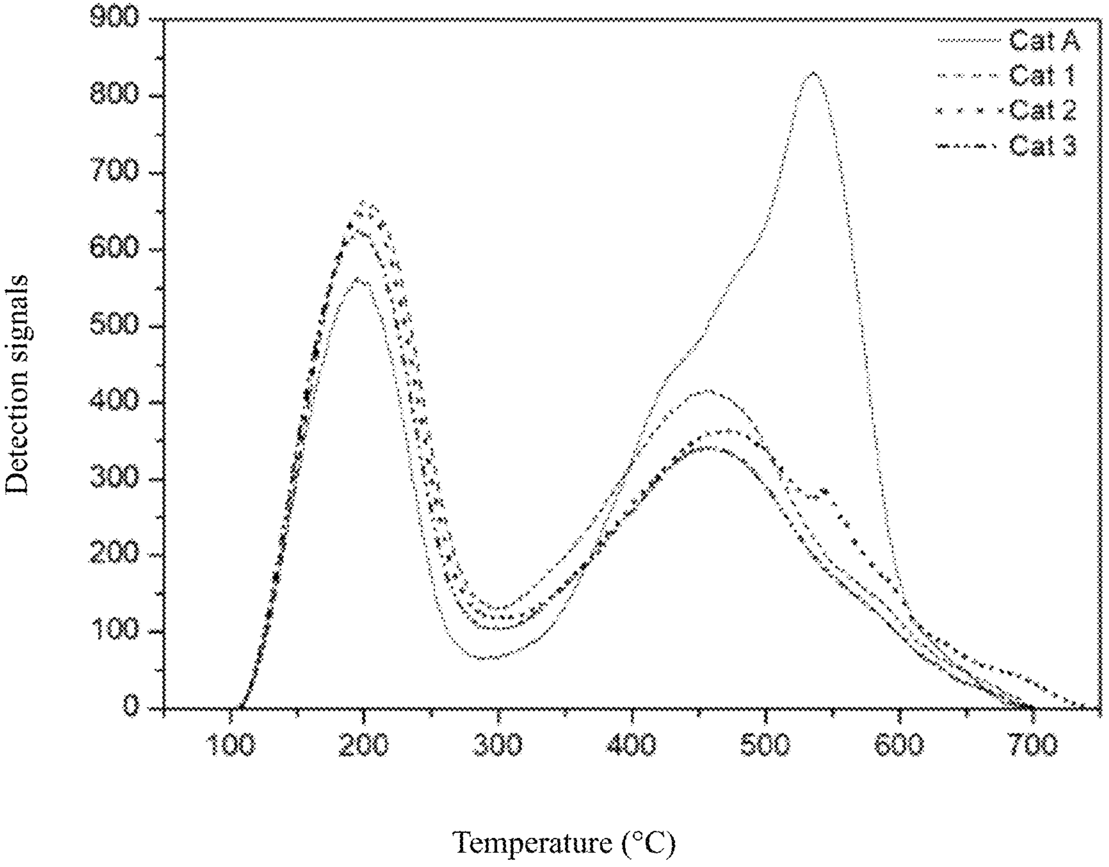
FIG. 3 shows the acidity of the sample according to the invention and the comparative sample.

Note:
$S_{BET}$: specific surface area; $S_{ext}$: external surface area; $V_{total}$: total pore volume; $V_{meso}$: mesopore volume FIG. 3 shows the acidity of the catalyst according to the invention and the comparative sample. It was found that the sample according to the invention had less acidity than the comparative sample.

In order to study the effect of the catalyst, which was the hierarchical zeolite and had metal inside its structure, on the production efficacy of light olefins from catalytic cracking for the hydrocarbon having 4 to 7 carbon atoms, different catalysts according to the invention were subjected to study with the comparative sample. The results are shown in FIG. 4 and FIG. 5.

Figure 4:
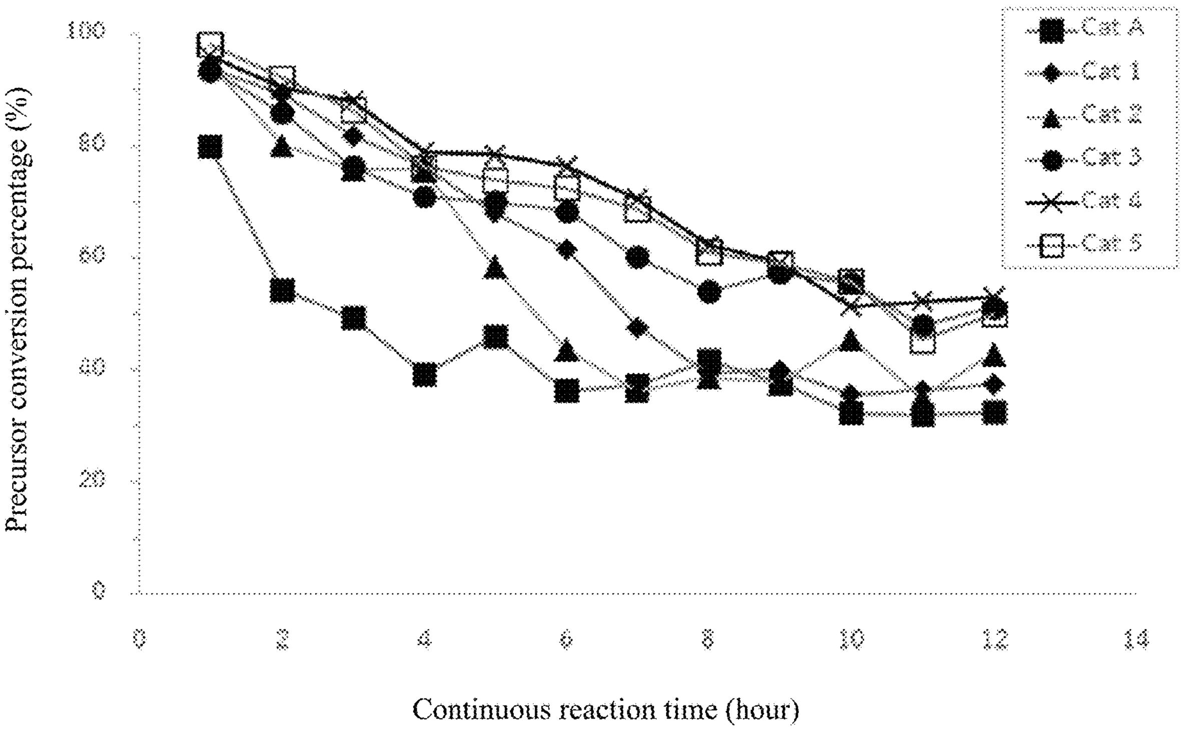
FIG. 4 shows the conversion percentage of reactant to product of the sample according to the invention and the comparative sample for the catalytic cracking of pentane.

FIG. 4 shows the conversion percentage of reactant to product of the sample according to the invention and the comparative sample for the catalytic cracking of pentane. It was found that the sample according to the invention gave better efficacy than the comparative sample. Especially, it was found that the structure of the catalyst according to the invention significantly reduced the catalyst deactivation.

Figure 5:
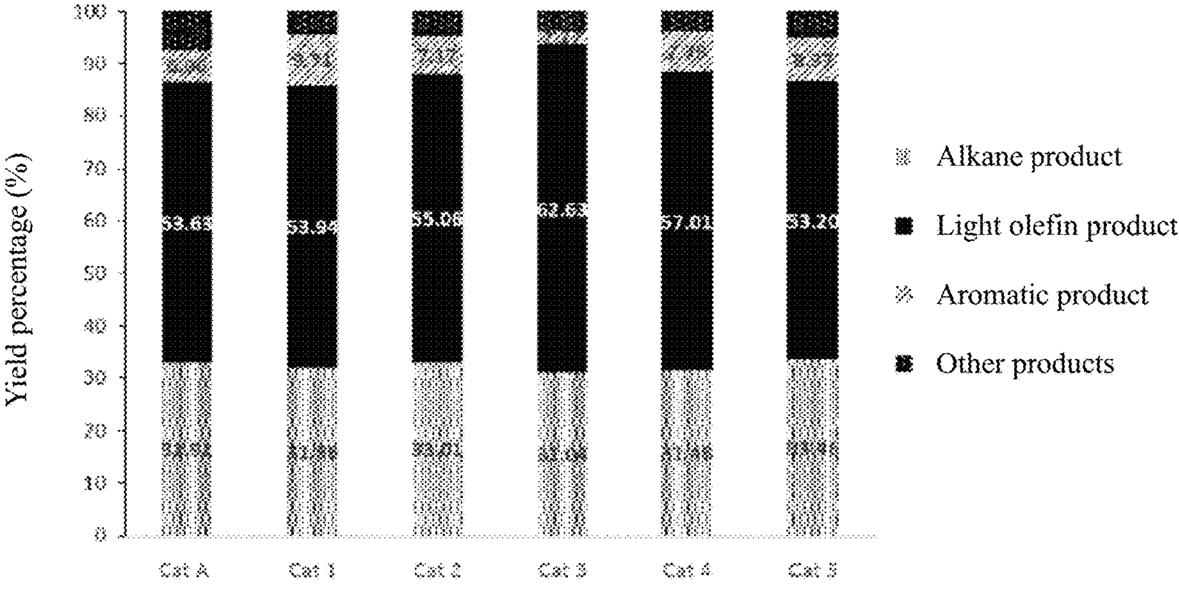
FIG. 5 shows the product selectivity of the sample according to the invention and the comparative sample for the catalytic cracking of pentane at the conversion percentage of reactant to product about 50%.

FIG. 5 shows the product selectivity of the sample according to the invention and the comparative sample for the catalytic cracking of pentane at the conversion percentage of reactant to product about 50%. It was found that the sample according to the invention gave higher selectivity to light olefins comparing to the comparative sample.

From the results above, it can be said that the catalyst, which was hierarchical zeolite and had element having $2^+$ to $4^+$ oxidation state within its structure, give high conversion percentage of reactant to product and high selectivity to light olefins for the catalytic cracking of the hydrocarbon having 4 to 7 carbon atoms as stated in the objective of this invention.

BEST MODE OR PREFERRED EMBODIMENT OF THE INVENTION

Best mode or preferred embodiment of the invention is as provided in the description of the invention.

The invention claimed is:

1. A catalyst for producing light olefins from catalytic cracking of hydrocarbon comprising 4 to 7 carbon atoms, wherein said catalyst consisting of: a hierarchical zeolite having 8 to 10 silicon atoms arranged in ring and comprising 0.1 to 2 nm micropore, 2 to 50 nm mesopore, and more than 50 nm macropore, wherein the mesopore and macropore are 40% to 60% of the total pore volume, and wherein said hierarchical zeolite has a mole ratio of silica to alumina of 20 to 60; and an element having $2^+$ to $4^+$ oxidation state of 0.1 to 3% by weight of the catalyst, wherein said element is selected from germanium, zirconium, or boron.

2. The catalyst according to claim 1, wherein said hierarchical zeolite has a pore size of 0.35 nm to 0.54 nm.

3. The catalyst according to claim 1, wherein the hierarchical zeolite comprises 0.35 to 0.54 nm micropore and 2 to 10 nm mesopore.

4. The catalyst according to claim 1, wherein said zeolite is ferrierite.

5. The catalyst according to claim 1, wherein said element is germanium.

6. The catalyst according to claim 1, wherein said element is 0.2 to 1% by weight of the catalyst.

7. A process for producing light olefins, comprising contacting hydrocarbon having 4 to 7 carbon atoms to the catalyst according to claim 1 at a temperature of 550 to 650° C. and a pressure of 1 to 3 bars.

8. The process according to claim 7, wherein the hydrocarbon having 4 to 7 carbon atoms can be selected from butane, pentane, hexane and heptane.

9. The process according to claim 7, wherein the light olefins are selected from ethylene, propylene, or a mixture thereof.

* * * * *